United States Patent [19]

United States Patent [19]

DeWitt et al.

[11] 4,423,736
[45] Jan. 3, 1984

[54] METHOD FOR EVALUATION OF ERYTHEMA UTILIZING SKIN REFLECTANCE MEASUREMENTS

[75] Inventors: David P. DeWitt; Robert E. Hannemann; Barrett F. Robinson, all of West Lafayette, Ind.; Edward J. Hanley, Broken Arrow, Okla.

[73] Assignee: Purdue Research Foundation, West Lafayette, Ind.

[21] Appl. No.: 310,474

[22] Filed: Oct. 13, 1981

[51] Int. Cl.³ .............................................. A61B 6/00
[52] U.S. Cl. .................................... 128/633; 128/653; 128/743
[58] Field of Search ................. 128/633, 637, 653, 743

[56] References Cited

U.S. PATENT DOCUMENTS 4,029,085 6/1977 DeWitt et al. ...................... 128/633
4,267,844 5/1981 Yamanishi .......................... 128/633

FOREIGN PATENT DOCUMENTS 19478 11/1980 European Pat. Off. ............ 128/633
2417433 10/1975 Fed. Rep. of Germany ...... 128/743
2744705 4/1979 Fed. Rep. of Germany ...... 128/633
2745297 4/1979 Fed. Rep. of Germany ...... 128/743

OTHER PUBLICATIONS

Ballowitz et al., "Spectral Reflectance of the Skin," Biol. Neanate, vol. 15, pp. 348–360, (1970).

Primary Examiner—Kyle L. Howell
Assistant Examiner—John C. Hanley
Attorney, Agent, or Firm—O'Rourke & Harris

[57] ABSTRACT

A method is disclosed for evaluating erythema utilizing skin reflection measurements. By collecting and analyzing data representative of both normal and erythematous skin utilizing reflectance spectra within a range of 400 to 700 nm, distinctive spectral features of erythema have been identified. A relationship representing a function of normal and erythematous skin reflectance at three specific wavelengths (500 nm, 550 nm, and 595 nm) was developed to provide an absolute measure of the vascular response of the skin, which measure is independent of pigmentation characteristics of the skin and takes into consideration normal fluctuations in skin color. By varying the exposure of the skin to radiation from a predetermined source and then measuring the reflectance of the skin at particular time periods and at a plurality (preferably three) of different wavelengths, the relative changes in superficial blood volume due to erythema are isolated. The method is thus useful for monitoring dosage dependence and time response of erythema, and is particularly well suited, for example, for determining sensitivity of skin to ultraviolet radiation, evaluation of sun screening agents and/or screening of individuals for susceptibility to irritation and/or irritants.

15 Claims, 11 Drawing Figures

METHOD FOR EVALUATION OF ERYTHEMA UTILIZING SKIN REFLECTANCE MEASUREMENTS

FIELD OF THE INVENTION

This invention relates to a method for evaluating erythema and, more particularly, relates to a method utilizing skin reflectance measurements for evaluating erythema.

BACKGROUND OF THE INVENTION

Erythema is reddening of the skin as a result of exposure to ultraviolet radiation (typically from the sun or other sources) or as a result of skin irritation (typically by exposure to chemical or mechanical agents). When such reddening of the skin is due to the exposure to the sun, the erythema is commonly called sunburn.

Although the histology and etiology of ultraviolet erythema has been studied in considerable detail, the phenomena is quite complex and is not as yet thoroughly understood. It is generally agreed, however, that ultraviolet radiation initiates a photochemical reaction in the epidermis which results in the liberation of a vasodilating substance or substances. This mediator substances migrates to the local capillaries and causes dilation, and the redness observed is attributable to an increased blood volume in the superficial blood vessels, mainly the subpapillary venules.

Prior studies of ultraviolet erythema have been hampered by the inability to quantitatively characterize the condition. Various visual grading scales and color comparison schemes have heretofore been employed in attempts to define the extent of vascular response to the photoactinic stimulus. In these methods, uncertainties have been found to arise due to the environmental lighting conditions, skin pigmentation characteristics, the experience of the observer and/or other factors which prevent quantitative and reproducible assessment of the condition.

It has been heretofore suggested that erythema could be characterized by evaluation of the local skin reflectance before and after ultraviolet exposure. While such approaches have been quantitative and found to be adequate in certain applications, the change in reflectance does not provide an absolute definitive measure of the degree of erythema. Instead, reflectance values depend upon the specific wavelengths considered and are biased by the local skin pigmentation. More specifically, the skin reflectance approach has heretofore been limited by the inability to relate the reflectance measure to a meaningful physiologic quantity such as blood content.

With respect to prior art patents, a device and method for detecting an abnormality of an organ or tissue is described in U.S. Pat. No. 4,213,462 to include an optical assembly for directing radiation toward an organ or tissue under a predetermined pressure and detecting reflected radiation to form electrical signals which are processed to provide an indication of the abnormality.

An ear oximetry process and apparatus is shown, by way of example, in U.S. Pat. No. 4,086,915 to include a non-invasive arrangement for detecting oxygen saturation of the blood through use of radiated and reflected light.

In addition, a process and apparatus for determining bilirubin concentration of a patient is described in U.S. Pat. No. 4,029,085, and an instrument for detecting jaundice is described in U.S. Pat. No. 4,267,844. In both instances, a non-invasive arrangement for emitting radiation at the skin of a patient and receiving radiation reflected from the skin is utilized to provide electrical signals that are processed to establish the presence of jaundice in the patient.

SUMMARY OF THE INVENTION

This invention provides a method for evaluating erythema utilizing skin reflectance measurements, and, more particularly, provides a method for evaluating erythema utilizing skin reflectance measurements made at a plurality of different wavelengths (preferably at least three).

It is therefore an object of this invention to provide a method for evaluating erythema.

It is another object of this invention to provide a method for evaluating erythema utilizing skin reflectance measurements.

It is still another object of this invention to provide a method for evaluating erythema using a plurality of different wavelengths to achieve reflectance measurements.

With these and other objects in view, which will become apparent to one skilled in the art as the description proceeds, this invention resides in the novel construction, combination, arrangement of parts and method substantially as hereinafter described, and more particularly defined by the appended claims, it being understood that such changes in the precise embodiment of the hereindisclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figure 1:
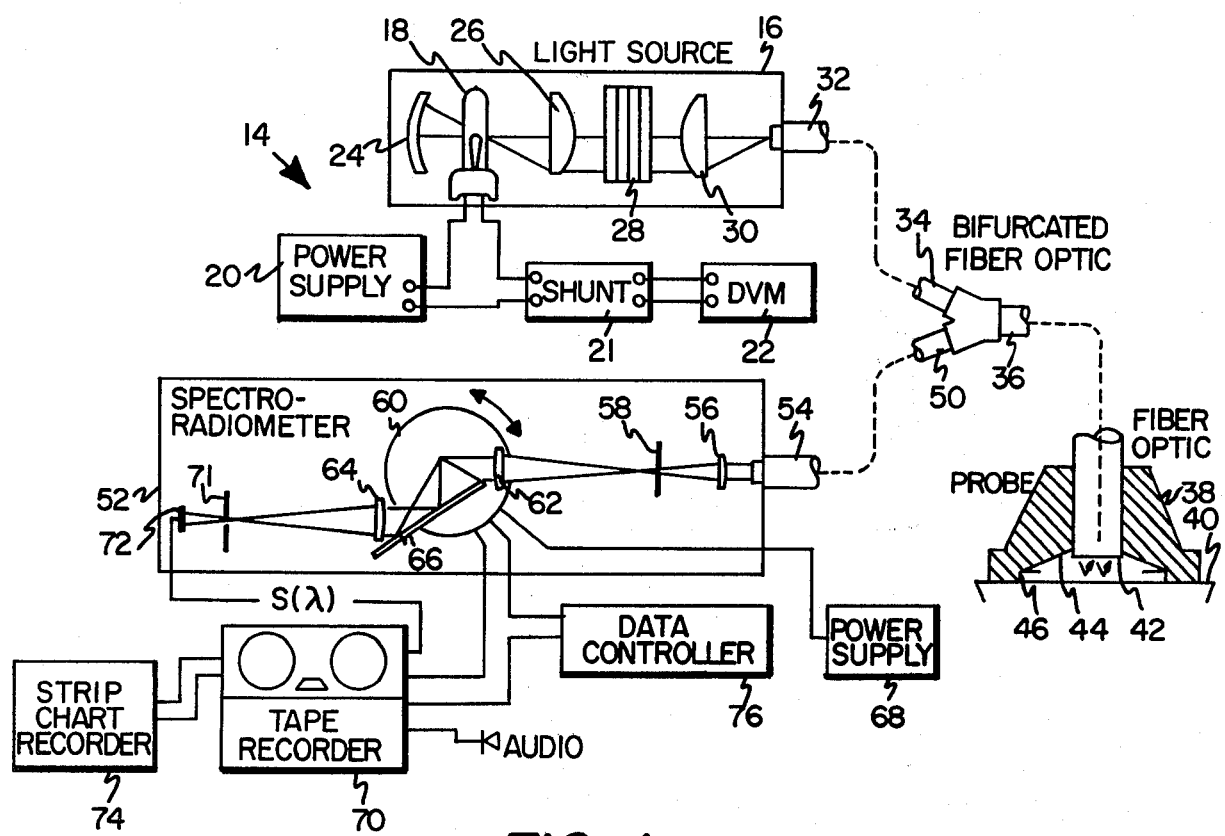
FIG. 1 is a schematic and block diagram of apparatus useful in measuring skin reflectance at a plurality of different frequencies.

An apparatus 14 from measuring the spectral reflectance of the skin of a patient is shown in FIG. 1. The apparatus is designed for rapid measurement (about 3.6 seconds/scan) of the absolute reflectance from 400 to 700 nm with moderate spectral resolution (about 10 nm).

As shown in FIG. 1, apparatus 14 includes a light source 16 shown to include a lamp 18 connected with power supply 20 and through shunt 21 to DVM 22. Light source 16 also includes a reflector 24, lens 26, filters 28, lens 30, and coupler 32 connected with the input leg 34 of bifurcated fiber optic 36.

Fiber optic 36 terminates at probe 38 adapted to be brought into contact with the skin 40 of a patient so that the end 42 of the probe is recessed from skin 40 so that a cavity is formed by conical inner wall 44 and ring 46 adapted to engage the skin 40 of the patient.

The radiation reflected from probe 38 is coupled through output leg 50 of fiber optic 36 to spectro-radiometer 52. As shown, leg 50 is connected with coupler 54 and the reflected radiation is coupled through lens 56 and focusing plate 58 to rotatable element 60 having lens 62, lens 64 and prism 66. Element 60 is also connected with power supply 68 and tape recorder 70, which also receives a $S(\lambda)$ signal from element 60 through focusing plate 71 and detector 72. Tape recorder 70 is also connected with strip chart recorder 74, and element 68 and tape recorder 70 are connected with data controller 76.

While the device shown in FIG. 1 may be utilized to measure skin reflectance in accordance with the method of this invention, other devices may also be utilized such as, for example, the device shown in U.S. Pat. No. 4,029,085, which is incorporated herein by reference, or the device shown in U.S. patent application entitled "Apparatus and Method for Determining a Condition from Measurement of Three or More Wavelengths" by DeWitt, et al., which application is owned by the assignee of this invention, is filed concurrently herewith, and is also hereby included by reference herein.

The development of erythema depends upon the dosage and spectral quality of the inciting ultraviolet radiation relating to the radiation dose being the product of the intensity and exposure time. Erythema has been observed to obey reciprocity within the usual range of clinical testing. A barely perceptible erythema is often used as a convenient measure of the ultraviolet dosage, and is commonly referred to as the minimal erythema dose (MED) the level of which is determined by exposing the skin to a series of increasing doses of radiation from a fixed source. This threshold dose concept is useful in comparison of the sensitivity of different skins as well as the effectiveness of radiation of different wavelengths in producing erythema.

Figure 2:
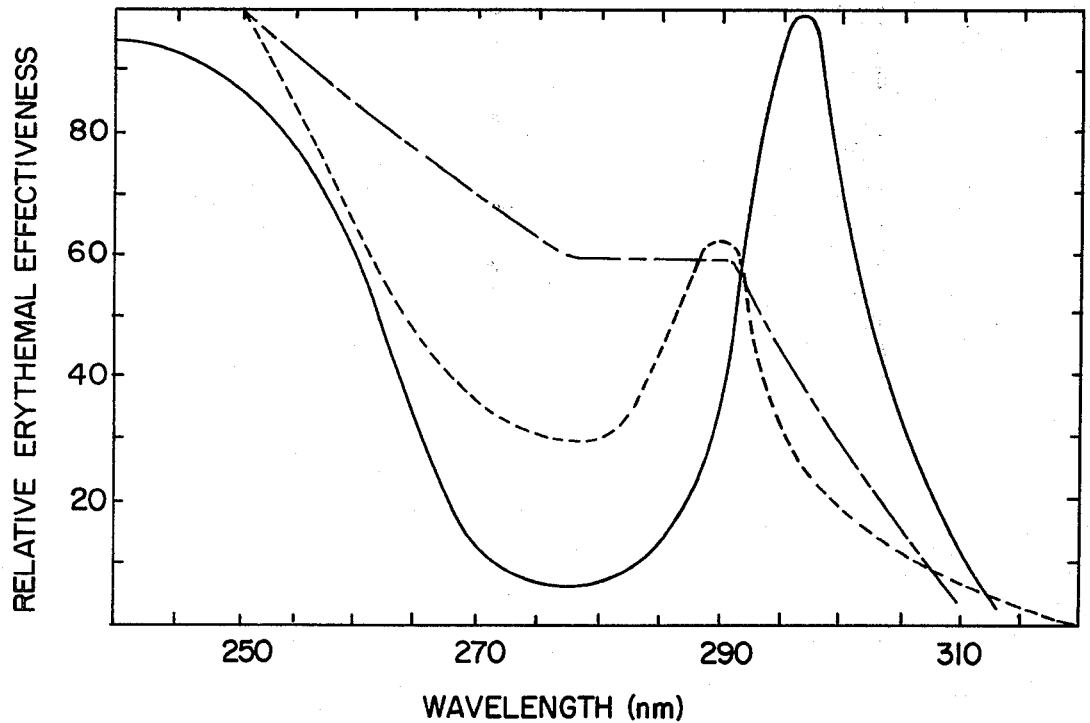
FIG. 2 is a typical erythema action spectra.

The action spectrum for erythema represents the relative effectiveness of equal amounts of energy at different wavelengths in producing erythema. Spectra representative of curves as heretofore reported in the literature are presented in FIG. 2. The erythema action spectrum is determined by using monochromatic radiation of varying wavelengths to elicit an MED response with the relative effectiveness being the reciprocal of the threshold dosage.

The shape of the action spectrum will vary depending upon the specific sensitivity of the particular skin to be monitored, the spectral resolution of the monochromator, and the criteria used for a minimal erythema. The basic character, however, is common to most determinations and several standardized erythema spectra have been heretofore proposed. The erythemagenic spectrum, however, is now generally considered to include wavelengths between 250 and 300 nm with a flat maximum at 250 nm, a minimum at 280 nm and a sharp peak at about 297 nm. Radiation in the 320 to 420 nm range will also elicit an erythema reaction, however, and the erythemal effectiveness in this waveband is about three orders of magnitude smaller than the effectiveness at 297 nm.

The vascular response which follows ultraviolet irradiation is essentially biphasic. An initial faint erythema may appear during exposure which tends to disappear shortly thereafter. This early phase is followed, after a latent period, by a prolonged delayed phase of erythema. Ordinarily, the delayed erythema appears 2 to 6 hours after exposure, reaches a maximum intensity in 12 to 24 hours and fades gradually over a period of days. Increasing the radiation dose elicits a more severe response: the latent time is reduced, the maximum redness occurs later and with increased intensity and the erythema persists longer. Erythema is typically followed by tanning which becomes noticeable two or three days after irradiation.

The erythema reactions due to wavelengths of 250 to 260 nm, 290 to 320 nm and 320 to 400 nm appear to be the result of three separate processes: the erythema resulting from irradiation using these wavebands are often referred to as UV-C, UV-B and UV-A erythema due to the traditional subdivision of the ultraviolet spectrum. Several basic differences are commonly observed which distinguish the UV-C and UV-B erythema: (1) the erythema caused by short wavelength irradiation appears and fades more quickly while the erythema resulting from longer wavelength irradiation appears later and persists longer, (2) UV-C erythema is pink while that produced by longer ultraviolet radiation is darker and redder, and (3) the UV-B erythema is greatly intensified as the dose is increased while the shorter wavelength erythema exhibits much less intensification with increasing dosage. Additional evidence supports the existence of two different mechanisms for UV-C and UV-B erythema, however, the specific reactions have not been isolated. Although both UV-A and UV-B radiation can induce clinically similar erythema response, it has recently been established that histologically the erythemas are not alike.

When subjects are exposed to solar radiation, the most effective wavelength band for producing erythema has been found to be 300 to 307.5 nm. Weak erythemagenic radiation of wavelengths 310 to 320 nm also contribute to development of sunburn since the relative intensity of these wavelengths in the solar spectrum is large in comparison with the 300 to 307 nm portion. Mild sunburn can also be induced by wavelengths in the 320 to 420 nm region, but the energy required to elicit erythema is so large that this region of the solar spectrum has generally been considered innocuous to normal human skin. Recent evidence, however, indicates that prexposure or post-exposure of the skin to UV-C ultraviolet will enhance the sunburn effects of the shorter wavelengths.

The observed gross effect of ultraviolet erythema upon skin color is reddening due to the increase in red blood in the dilated superficial vessels and this effect is independent of the mechanism of the erythema. Another consequence of exposure to ultraviolet radiation is the familiar increase of melanin pigmentation of the skin generally known as tanning. The increase in melanin is due to two distinct photobiologic processes: immediate pigment darkening and primary melanization. The immediate pigment darkening begins immediately upon exposure of the skin to light and the darkening fades rapidly after the end of irradiating with the color of the skin returning to normal within the next 6 to 8 hours although occasionally residual hyperpigmentation may persist for as long as 24 hours. Tanning due to primary melanization involves production of new melanosomes and therefore appears slowly after an interval of 48 to 72 hours and persists for an indefinite period.

While it has been demonstrated that skin color can be determined quantitatively by measurement of the skin spectral reflectance characteristics, and previous studies have indicated that exposure to ultraviolet light causes characteristic alterations in the skin which are recognizable in the reflectance spectrum, a heretofore major deficiency of the skin reflectance studies has been the inability to relate the reflectance measure to a meaningful physiologic measure such as blood content. In this invention, with systematic study of the skin reflectance characteristic, intepretation of spectra using the physical skin model and consideration of the optical properties of pertinent skin constituents, optimal parameters for quantitative and meaningful evaluation of ultraviolet erythema have been determined.

Quantitative evaluation of erythema by skin reflectance analysis requires a method of relating the measured spectral reflectance to a physically meaningful parameter. The approach is to use a photo-diffusion model which treats photons as particles which are scattered and absorbed throughout the optical medium. If the various components are uniformly distributed throughout the medium, the bulk optical coefficients of the composite material, k and w, can be reasoned to be a linear combination of those of the constituents, weighted by their volume fraction as follows:

$$k = \sum_i k_i V_i \quad (1)$$

$$w = \sum_i w_i V_i \quad (2)$$

where $k_i$, $w_i$, and $V_i$ are the scattering coefficient, absorption coefficient and volume fraction of component i, respectively. This supposition is possible due to the linearity in the basic assumption of the model.

The basic optical parameter defined by the model is the Kubelka-Munk function, $\xi$, given as $$\xi = \frac{w}{k} = \frac{R}{2} + \frac{1}{2R} - 1 \quad (3)$$

where w and k are the bulk absorption and scattering coefficients, respectively, and R is the skin reflectance. Note that all of these parameters may be written on a spectral basis. This equation establishes the relationship between the measurable skin reflectance and the absorption and scattering characteristics of the skin.

Figure 4:
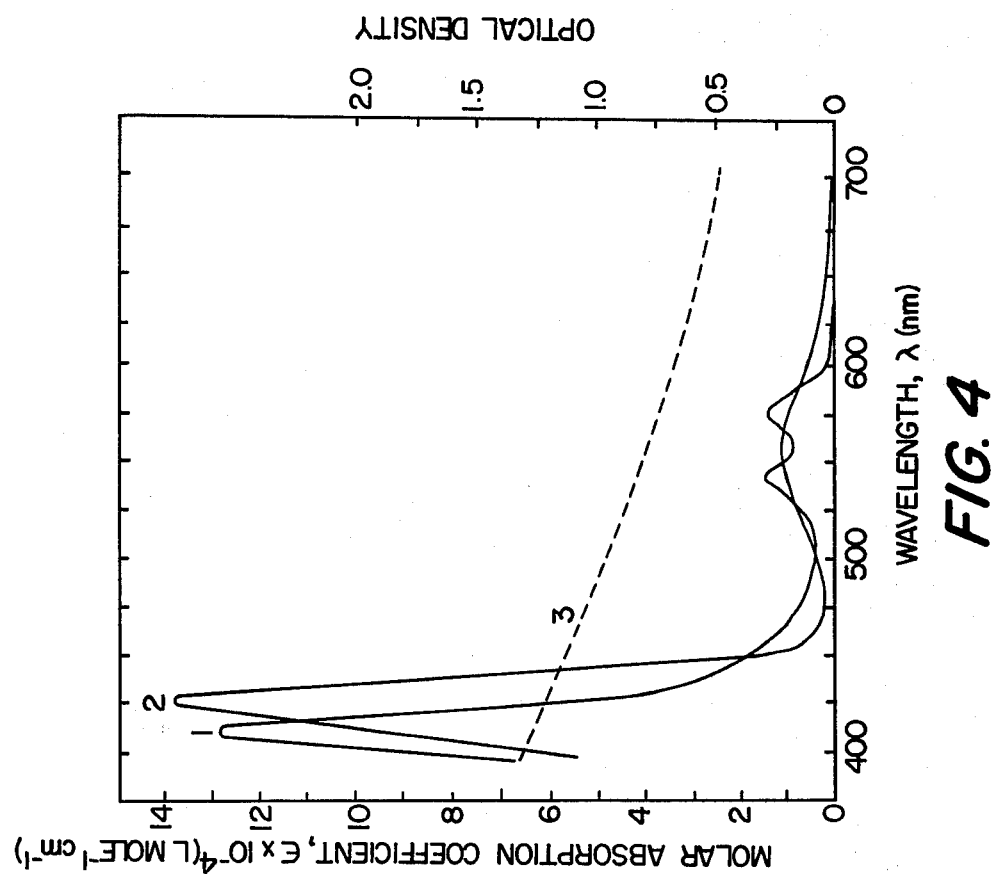
FIG. 4 is a spectral absorption characteristic of hemoglobin and melanin pigments.
Figure 3:
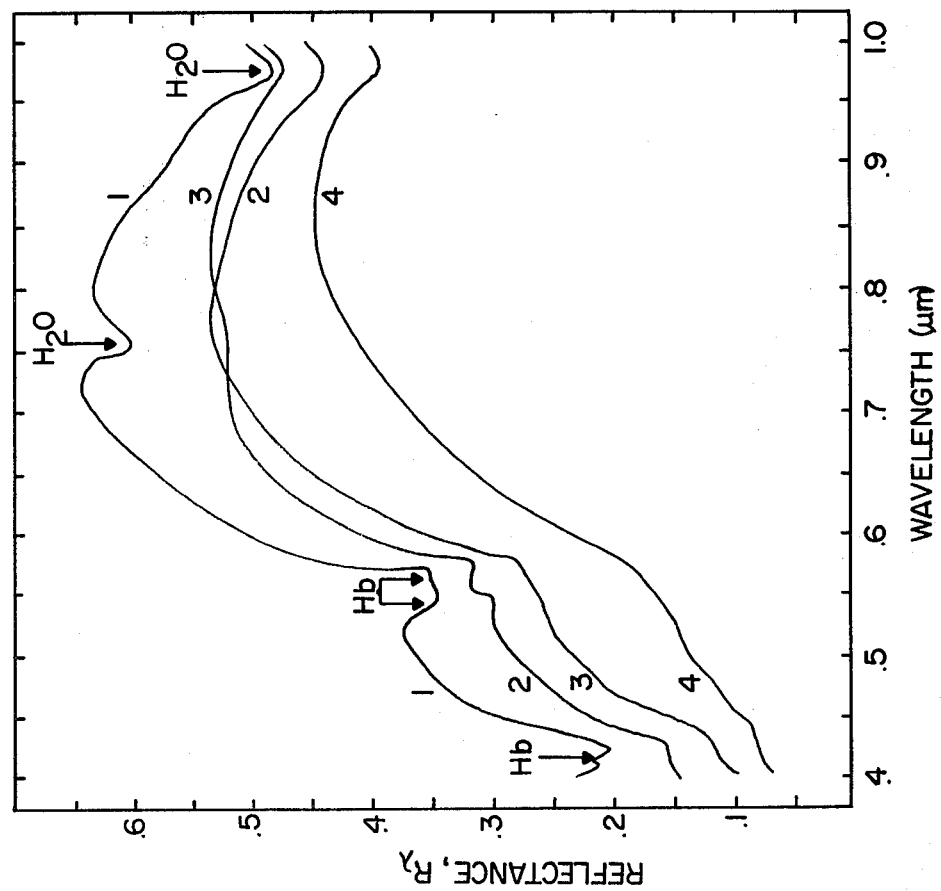
FIG. 3 is a skin reflectance spectra of the forearm of individuals of various races.
Figure 6:
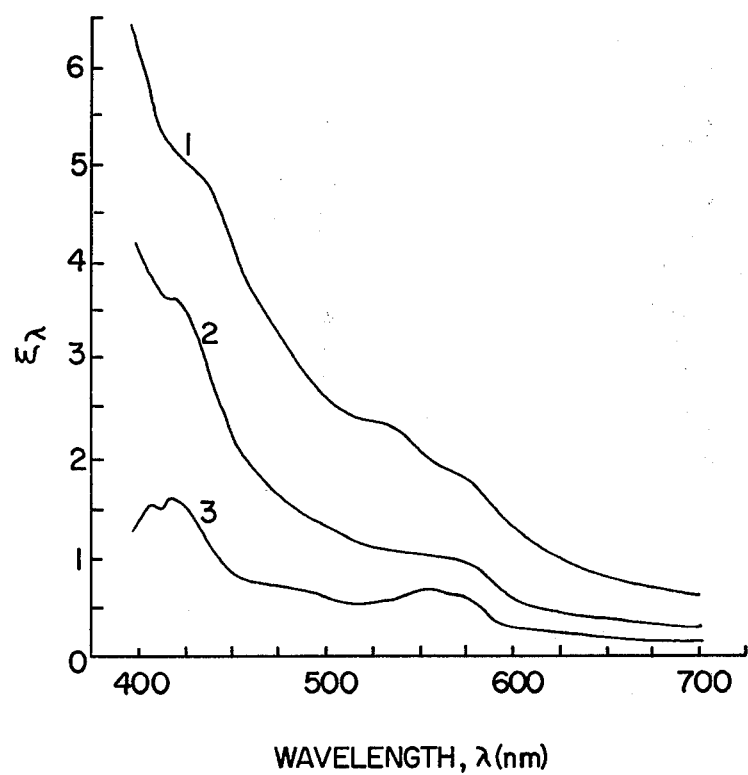
FIG. 6 shows spectral Kubelka-Munk function, $\xi\lambda$, of skin for individuals of varied complexions.

The skin $\xi$-spectra of three individuals is presented in FIG. 6 wherein curve 1 is that of a dark negro, curve 2 is that of a light negro, curve 3 is that of a light caucasian, with FIG. 6 having been derived by transformation of the reflectance spectra of FIG. 3 wherein curve 1 is that of a light caucasian, curve 2 is that of a Japanese, curve 3 is that of a light negro, and curve 4 is that of a dark negro. Assuming that the skin scattering coefficient is relatively insensitive to wavelength, the $\xi$-curves represent the relative absorption characteristics of the skin. This can be verified quantitatively by comparison of the $\xi$-spectra to the skin pigment absorption characteristics of FIG. 4 with consideration of the super-position principle. In FIG. 4, curves 1 and 2 are absorption coefficient curves of oxyhemoglobin and hemoglobin, respectively, while curve 3 is an optical density curve of melanin. Note that a darker complexioned individual possesses a larger volume fraction of melanin in the skin and would be expected to have larger values. These spectra qualitatively support the applicability of the simple skin model.

Physically, the redness of erythema is the result of an increase in the volume fraction of blood in the superficial tissue due to dilation of vessels. The bulk absorption coefficient is a linear combination of the absorption coefficients of the individual skin constituents weighted by their volume fraction (see Equations (1) and (2)). Thus, the increase in blood volume, $\Delta V_b$, due to erythema is linearly related to the normalized change in Kubelka-Munk function as follows:

$$\overline{\Delta \xi} = \frac{\xi_E - \xi_N}{\xi_N} = \frac{w_b \Delta V_b}{w} \quad (4)$$

where the subscripts E and N correspond to the erythemal and normal conditions, respectively. The characteristics of hemoglobin in the erythemal tissue are embodied in the blood-absorption coefficient, $w_b$, while w is the bulk absorption coefficient of the skin under normal conditions.

The normalized quantity, $\overline{\Delta \xi}$, represents the relative change in skin absorption due to erythema. Evaluation of this term on a spectral basis will demonstrate the relative sensitivity of specific wavelengths to changes in superficial blood volume. The $\overline{\Delta \xi}$ parameter does not provide a quantitative measure of erythema, however, since the influence of all skin absorption mechanisms will be evident in the denominator. Specifically, the variable melanin content of the skins will influence the sensitivity of this relation through the contribution of the pigment to the bulk absorption coefficient. Furthermore, since ultraviolet irradiation of skin also has the effect of stimulating melanin production, the contribution of melanin can bias results nonuniformly; this is particularly significant in serial erythema studies.

A normalized parameter, $\overline{\delta}(\lambda_1, \lambda_2, \lambda_3)$, was devised to provide an unbiased measure of erythema. This parameter, based upon the skin reflectance at three wavelengths, is defined as:

$$\overline{\delta}(\lambda_1,\lambda_2,\lambda_3) = \frac{\delta(\lambda_1,\lambda_2,\lambda_3)_E - \delta(\lambda_1,\lambda_2,\lambda_3)_N}{\delta(\lambda_1,\lambda_2,\lambda_3)_N} \quad (5)$$

where $$\delta(\lambda_1,\lambda_2,\lambda_3) = [\xi(\lambda_1)-\xi(\lambda_2)]+[\xi(\lambda_1)-\xi(\lambda_3)] \quad (6)$$

With consideration of the spectral absorption characteristics of the primary skin pigments of hemoglobin and melanin, it can be shown that $$\bar{\delta}(500,550,595) = \frac{\Delta V_b}{V_b} \quad (7)$$

where 500, 550 and 595 refer to wavelengths in nanometers and $V_b$ is the blood volume in the normal healthy tissue. Thus, this triple-wavelength parameter isolates the relative change in superficial blood volume due to erythema. Specific wavelengths in the above relation were selected on the basis of published absorption characteristics of hemoglobin and melanin.

As brought out hereinabove, apparatus for measurement of the spectral reflectance of skin in vivo is shown schematically in FIG. 1. In the normal mode of operation, the radiation source provides an illuminating flux which is transferred through one branch of a bifurcated fiber optic bundle to the target (i.e., the surface of the skin). Reflected flux is thus transmitted through the second branch of the fiber optic to a spectroradiometer where the radiation is dispersed and measured using a silicon photodiode. Reflected flux from the skin and a reflectance standard are observed and recorded on magnetic tape. During the subsequent computer processing of the observation, the absolute spectral reflectance of the skin is thus determined.

The experimental procedure involves two separate steps. The first involves the induction of erythema by exposure to ultraviolet light, while in the second step, the erythemal reaction is recorded via measurement of the local skin reflectance.

The light source was used to irradiate small areas, roughly 1 cm in diameter, on the middle back region of the subject. The back was a favorable experimental location since it presented a readily accessible, broad area of relatively uniform physical characteristics with abundant space for a number of exposure sites. The subject received a series of exposures in discrete dosage increments centered about an estimated MED, with exposures being controlled by an automated timer/shutter system. The estimated MED selection was based upon the subject's own evaluation of his sensitivity of sunburn and tanning and by visual evaluation of the pigmentation at the specific test sites. The exact number of exposures administered varied as experimental circumstances required. No dosage exceeded five MED, however, so that the subject experienced no discomfort, the only effects being erythema and possibly tanning.

On the second test day, twenty-four hours after irradiation, the site at which a minimally perceptible erythema (MPE) was observed was recorded at the minimal erythema dose (MED) of the subject. Although this determination of the erythemal threshold was inexact, the visual measure provided a consistent reference point on the erythemal scale. This measure was useful in adjusting dosage to the tolerance level of the individual and served as a common factor for normalization of results in studies where, for example, erythema time response rather than dosage tolerance was the parameter of interest.

The skin reflectance measurement system of FIG. 1 was utilized to monitor the spectral reflectance of the skin at selected test sites. Since the physical model dictated that the change in skin reflectance was the important parameter for evaluation of erythema, the reflectance of the test site and that of a closely adjacent nonirradiated skin area was measured for each experimental observation. This procedure implicitly accounts for normal fluctuations in the skin reflectance characteristics.

Generally, two replications of the skin reflectance measurements were performed at each test site and the reported values represent the average of these results. Occasionally, a given skin spectrum was observed to be elevated relative to comparable spectra and this was attributed to problems arising from probe-pressure. In this event, the spectral values were reduced by an appropriate correction factor before data transformations were performed. Also, an occasional reflectance measure was rejected on the basis of its exhibiting uncharacteristic or peculiar spectral characteristics; these anomalies are due to instabilities in the measurement procedure. Thus, the experimental procedure included the editing of data to this limited extent.

The experimental investigation was divided into three phases: resolution of the distinctive spectral reflectance features of erythema, examination of the influence of ultraviolet dosage in producing erythema and determination of the characteristic time response of the skin after ultraviolet irradiation.

The first experimental phase involved measurement of the spectral reflectance of the skin of a caucasian subject twenty-four hours after exposure to ultraviolet light. The spectral characteristics of the skin were evaluated for determination of optimal wavelength regions for monitoring erythema and results are presented for three ultraviolet dosage levels.

In the second phase, a series of twelve incremental dosages were administered to the subject and the reflectance of each test site was measured twenty-four hours after the ultraviolet irradiation. The reflectance spectra of selected sites for this subject were also monitored daily over a period of two weeks to provide information concerning the recovery of the skin with time relative to the erythema dosage. Additional data acquired from a larger sample population of 22 individuals were also discussed in this final phase. The sample population is limited to caucasians since this group accounts for the preponderant incidence of actinic damage.

Figure 5:
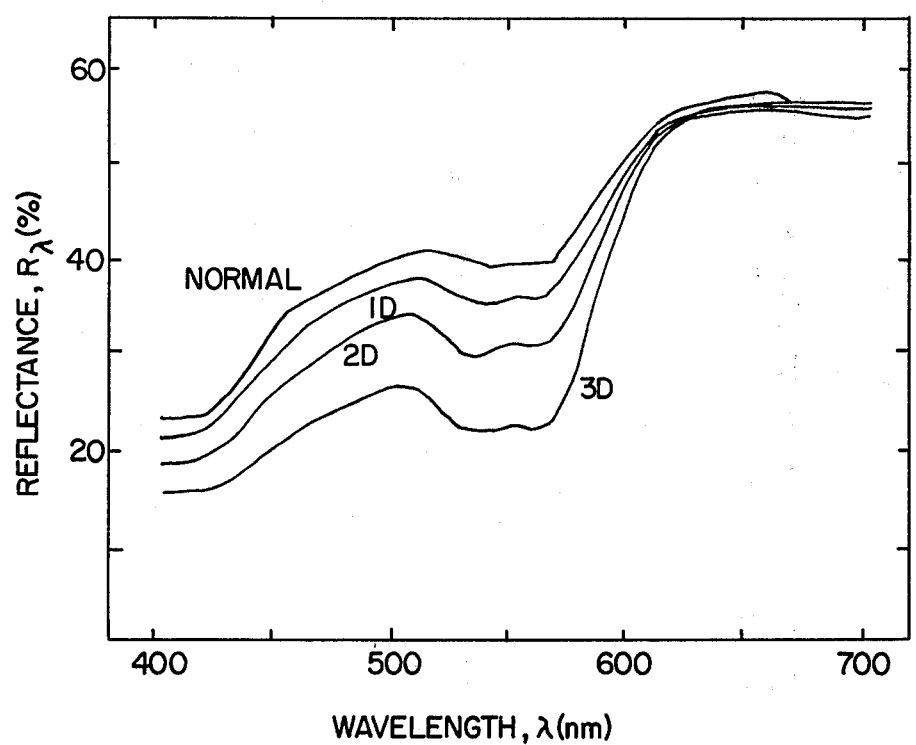
FIG. 5 shows spectral reflectance of normal skin and erythema for three ultraviolet dosages.

Reflectance spectra were acquired for normal skin and skin exposed to incremental doses of ultraviolet light using the procedures previously described. The spectral reflectance of the unexposed skin and that of three irradiated sites on a single subject determined twenty-four hours following exposure are shown in FIG. 5. Erythema is observed to reduce the reflectance for visible wavelengths shorter than 600 nm; this increased absorption at short wavelengths is responsible for the reddened visual impression characteristic of sunburn. The increased absorption is attributable mainly to an increased volume of blood in the superficial tissue resulting from dilation of vessels. The reflectance of skin at wavelengths longer than 600 nm unaffected by erythema since hemoglobin, which dominates the blood absorption characteristic, absorbs relatively poorly in this region. Note that since the observations were made only twenty-four hours after ultraviolet exposure, the melanin content of the skin has not had time to change appreciably.

In FIG. 5, the notation 1D, 2D and 3D refer to three incremental ultraviolet dosage levels. Dose "D", in this case, is a two minute exposure to the ultraviolet source with the intensity set at 0.15 mW cm$^{-2}$ of UV-B and 7.8 mW cm$^{-2}$ of UV-A as measured using an International Light Co. Model IL 700 Research Radiometer equipped with appropriate filters; doses 2D and 3D correspond to four and six minute exposures, respectively. The MED for this subject, using the criteria of minimal perceptible erythema at twenty-four hours post irradiation, was observed for a 90 second exposure; the two minutes exposure site was the minimum perceptible dosage with clearly defined boundaries.

According to the physical model, Equation (4), a change in the optical absorption of the skin can be isolated by evaluating the change in Kubelka-Munk function, $\Delta \xi_\lambda$, where $$\Delta \xi_\lambda = (\xi_E - \xi_N)_\lambda = \frac{w_b \Delta V_b}{k} \tag{8}$$

Figure 7:
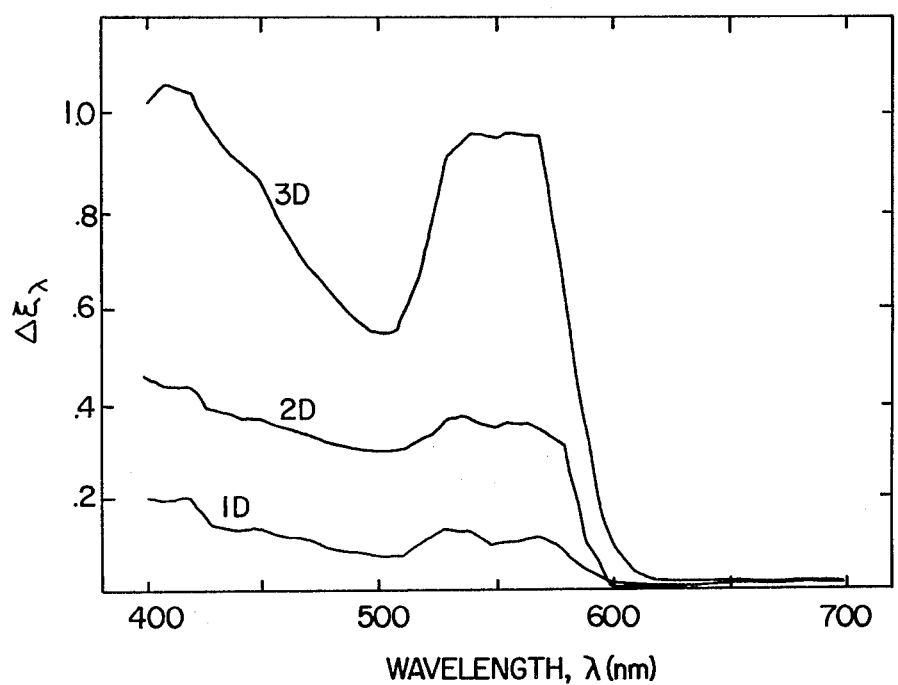
FIG. 7 shows the change in the Kubelka-Munk function, $\Delta\xi\lambda$, for three dosages of erythema.

This difference parameter is plotted in FIG. 7 (which should be compared with the normal spectral Kubelka-Munk function as shown in FIG. 6) for the three levels of erythema shown in FIG. 5. The shape of the $\Delta \xi_\lambda$ spectra is similar to the absorption spectra of hemoglobin as anticipated although the absorption bands are somewhat broadened due to the limited resolution of the skin reflectance measurement system. The relative absorption curves of FIG. 7 appear to be most similar to the oxyhemoglobin absorption spectrum. This is not unexpected since, under normal conditions, arterial and venous blood are about 95 and 70 percent oxygenated, respectively. The absorption band in the 400 nm region is considerably less prominent in the $\Delta \xi_\lambda$ spectrum than in the oxyhemoglobin absorption spectrum shown in FIG. 4. This indicates that the scattering coefficient is not independent of wavelength but rather increases substantially at short visible wavelengths; recall that the scattering coefficient is the denominator of the $\xi$ factor. At longer visible wavelengths, the scattering coefficient appears to be more nearly constant.

To determine the wavelengths which are most significant in interpretation of erythema spectra, it is useful to examine the normalized change in Kubelka-Munk function, $\overline{\Delta \xi_\lambda}$, where, through Equation (4):

$$\overline{\Delta \xi_\lambda} = \left| \frac{\xi_E - \xi_N}{\xi_N} \right|_\lambda = \left| \frac{w_b V_b}{w} \right| \tag{9}$$

Figure 8:
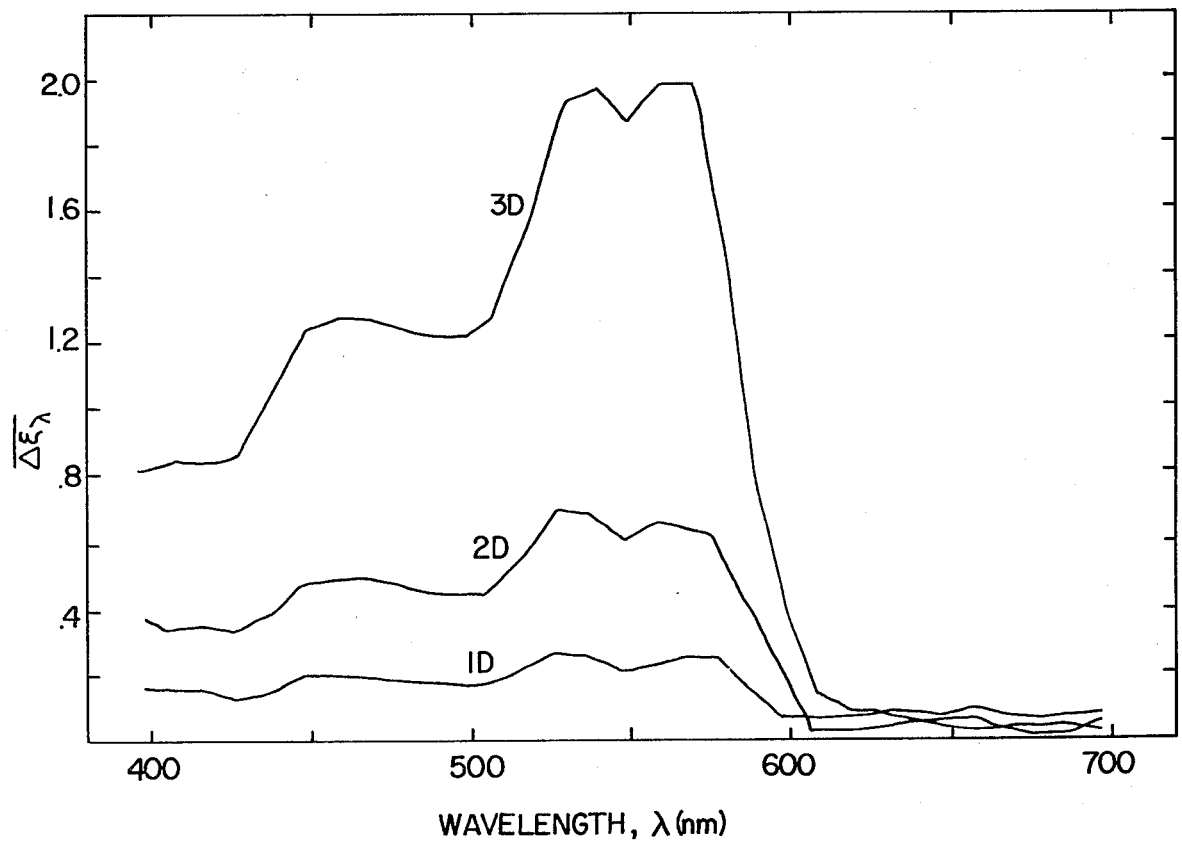
FIG. 8 shows the normalized change of the spectral Kubelka-Munk function, $\Delta\xi\lambda$, for three dosages of erythema.

This quantity, which represents the relative change in skin absorption due to the erythema, is plotted in FIG. 8 for the three erythema sites of the same subject. These curves illustrate that wavelengths in the 550 nm region are most responsive and thus most suitable for use in evaluation of erythema. The shorter wavelengths, near the 400 nm absorption band, are less sensitive to changes in superficial blood volume since the highly absorbing melanin pigment tends to mask the hemoglobin absorption mechanism in this region.

Overall, erythema is observed to have a dramatic influence upon the spectral reflectance of the skin. Specifically, erythema decreases reflectance of the skin in the oxyhemoglobin absorption bands; this corresponds to an increased superficial blood volume. The spectral quality of the erythema, within the experimental limits, is observed to be independent of the degree of erythema as induced by varying ultraviolet dosages. Finally, while the relative spectral responsivity of skin reflectance to erythema has been determined, it is apparent that normal optical mechanisms of the skin influence the sensitivity of this relationship; since skin properties exhibit considerable natural variation, quantitative evaluation of erythema by skin reflectance analysis requires elimination of these extraneous features.

For the purpose of examining the influence of ultraviolet dosage upon erythemal response, a subject was exposed to twelve successive levels of the ultraviolet radiation and the skin reflectance of each test site was measured after an interval of twenty-four hours. The exposure times of the twelve doses range from 45 seconds to 6 minutes with the source intensity set as previously reported. The dosage notation employed herein is consistent with that of the preceding section since the same subject was tested in both experiments.

The skin physical model dictates that the proper way to interpret erythema reflectance spectra is to evaluate a normalized $\delta$-type parameter $\overline{\delta}(\lambda_1,\lambda_2)$, defined in terms of two wavelengths as illustrated in Equation (5) for three wavelengths. This parameter, under ideal conditions, isolates the change in superficial blood volume as shown in Equation (7):

$$\delta(\lambda_1,\lambda_2) \simeq \frac{\Delta V_b}{V_b} \tag{10}$$

In view of the preceding results and considering the spectral characteristics of normal skin pigmentation, a variety of wavelength-pair combination will apparently be equally suitable for use in the erythema parameter, $\overline{\delta}(\lambda_1,\lambda_2)$.

Figure 9:
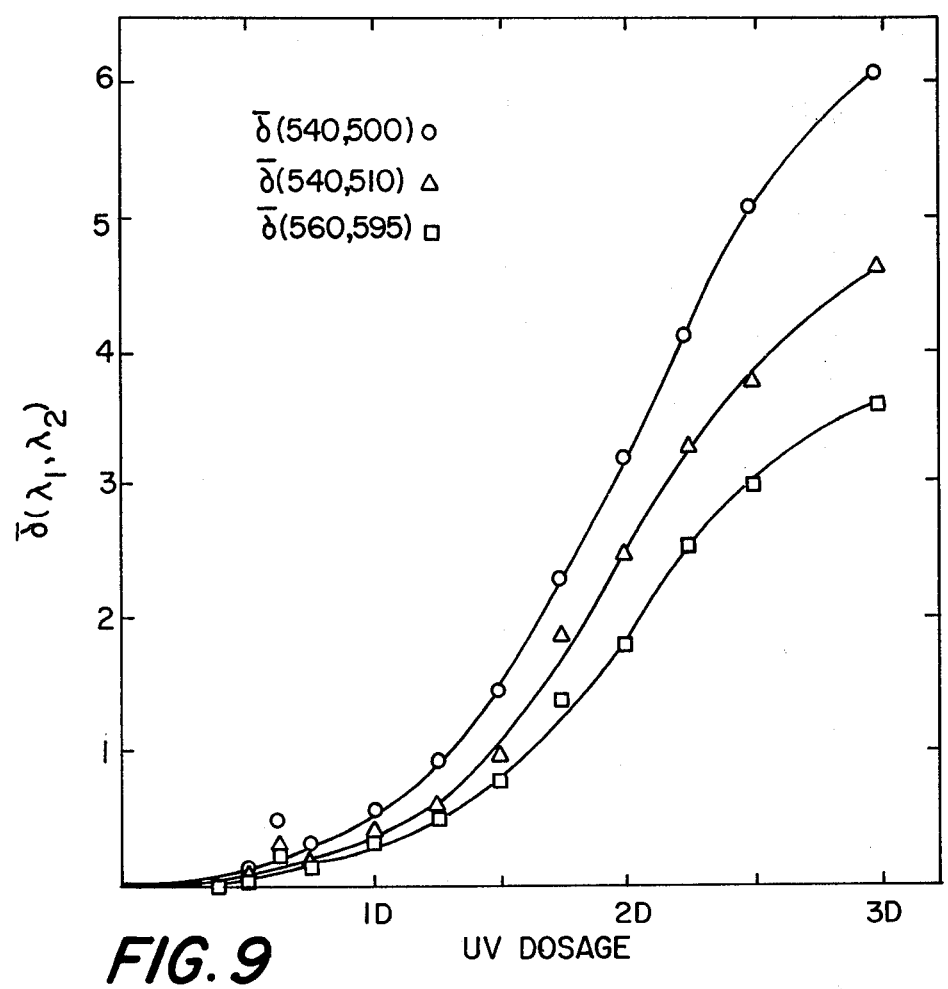
FIG. 9 shows the two wavelength erythema parameter, $\overline{\delta}(\lambda_1, \lambda_2)$, as a function of ultraviolet dosages for three wavelength pairs.

Experimental results for three wavelength-pairs are presented in FIG. 9. Note that spectral values at 595 nm are the average of associated 590 and 600 nm data; this procedure is taken to accommodate the reduced spectral resolution of the skin reflectance measurement system at these longer wavelengths where the reflectance characteristics are changing markedly.

If the selected $\overline{\delta}(\lambda_1,\lambda_2)$ parameters are effective in isolating the contribution of blood absorption in the skin reflectance measure, the three curves of FIG. 9 would be expected to be identical; this is not the case, however. The observed discrepancies are attributed to the inability of the two-wavelength model to completely eliminate the contribution of melanin pigment absorption. The influence of melanin is introduced in the denominator of the $\overline{\delta}(\lambda_1,\lambda_2)$ factor as follows $$\overline{\delta}(\lambda_1,\lambda_2) = \frac{(w_{\lambda_1} - w_{\lambda_2})_b V_b}{(w_{\lambda_1} - w_{\lambda_2})_b V_b + (w_{\lambda_1} - w_{\lambda_2})_m V_m} \tag{11}$$

Thus, since the absorption of melanin decreases continuously with increasing wavelength, when $\lambda_1 > \lambda_2$ the effect of melanin is to reduce the $\overline{\delta}(\lambda_1,\lambda_2)$ parameter and produce seemingly low results; similarly, when $\lambda_2 < \lambda_1$, the influence of melanin is to induce overly high results. This behavior is verified in FIG. 9 where the results for $\overline{\delta}(540,500)$ and $\overline{\delta}(540,510)$ are considerably above those of $\overline{\delta}(560,595)$. Also, the above relation indicates that the influence of melanin will be reduced by selecting closely adjacent wavelengths; comparison of the $\overline{\delta}(540,500)$ and $\overline{\delta}(540,510)$ curves substantiates this. The influence of melanin absorption is stronger in the $\overline{\delta}(540,500)$ data and therefore this function produces a higher apparent increase in blood volume than $\overline{\delta}(540,510)$. The actual degree of vasodilation is likely between the $\overline{\delta}(540,510)$ and $\overline{\delta}(560,595)$ values. Although the $\overline{\delta}$ parameters of FIG. 9 do not quantitatively described the erythemal vascular response, these results do support the applicability of the skin model; the consistency between the experimental results and the trends dictated by the model provide this support.

The experimental results of FIG. 9 also illustrate, albeit somewhat qualitatively, the essential characteristics of the dosage dependence of ultraviolet erythema. The curves indicate that dilation of vessels occurs only minimally for low ultraviolet dosages but increase dramatically with exposure level for moderate (>1MED) dosages. As the dosage is further increased, the rate of increase in vascularity is diminished; this tapering action is attributed to the fact that the superficial vessels have a maximum distension limit. As the dosage is further increased, it is anticipated that an increasing number of vessels will expand maximally and the measurable $\bar{\delta}$ parameter will asymptotically approach a limiting value. This limit may not be attainable in practice, however, since excessive ultraviolet dosages may have complicating detrimental effects such as desquamation.

Although the $\bar{\delta}(\lambda_1,\lambda_2)$ parameters are useful in interpretation of erythemal vascular response, it is desirable to have an absolute measure where the influence of melanin has been eliminated. This is important for comparison of results between individuals since subjects may exhibit wide natural variations in pigmentation. Furthermore, since ultraviolet irradiation of skin also has the effect of stimulating melanin production, the contribution of melanin can bias results nonuniformly; this is particularly significant in serial erythema studies. The effect of melanin can be removed from the $\bar{\delta}$ function by the use of weighting factors to account for the differences in optical coefficients at the two wavelengths or by introduction of additional spectral information. Since the optical characteristics of natural melanin have not been well established, the latter approach appears more appropriate. The procedure is simply to expand the present model to a three-wavelength $\bar{\delta}$ parameter, $\bar{\delta}(\lambda_1,\lambda_2,\lambda_3)$ where $$\bar{\delta}(\lambda_1,\lambda_2,\lambda_3) = \frac{\delta(\lambda_1,\lambda_2,\lambda_3)_E - (\lambda_1,\lambda_2,\lambda_3)_N}{\delta(\lambda_1,\lambda_2,\lambda_3)_N} \quad (12)$$

and $$\delta(\lambda_1,\lambda_2,\lambda_3) = [\xi(\lambda_1) - \xi(\lambda_2)] + [\xi(\lambda_1) - \xi(\lambda_3)] \quad (13)$$

As in development of Equation (9), the $\bar{\delta}(\lambda_1,\lambda_2,\lambda_3)$ parameter can be expanded by considering the contributions of blood and hemoglobin:

$$\frac{(w_{\lambda_1} - w_{\lambda_2})_b V_b + (w_{\lambda_1} - w_{\lambda_3})_b V_b}{(w_{\lambda_1} - w_{\lambda_2})_b V_b + (w_{\lambda_1} - w_{\lambda_3})_b V_b + (w_{\lambda_1} - w_{\lambda_2})_m V_m + (w_{\lambda_1} - w_{\lambda_3})_m V_m} \quad (14)$$

The wavelengths are chosen such that $\lambda_1$ is strongly responsive to hemoglobin absorption while the difference in melanin absorption coefficient between $\lambda_1$ and $\lambda_2$ is equal but opposite to the difference between $\lambda_1$ and $\lambda_3$. Under these conditions, the absorption coefficients in the last equation cancel and $\bar{\delta}(\lambda_1,\lambda_2,\lambda_3)$ reduces to $$\bar{\delta}(\lambda_1,\lambda_2,\lambda_3) = \frac{\Delta V_b}{V_b} \quad (15)$$

Figure 10:
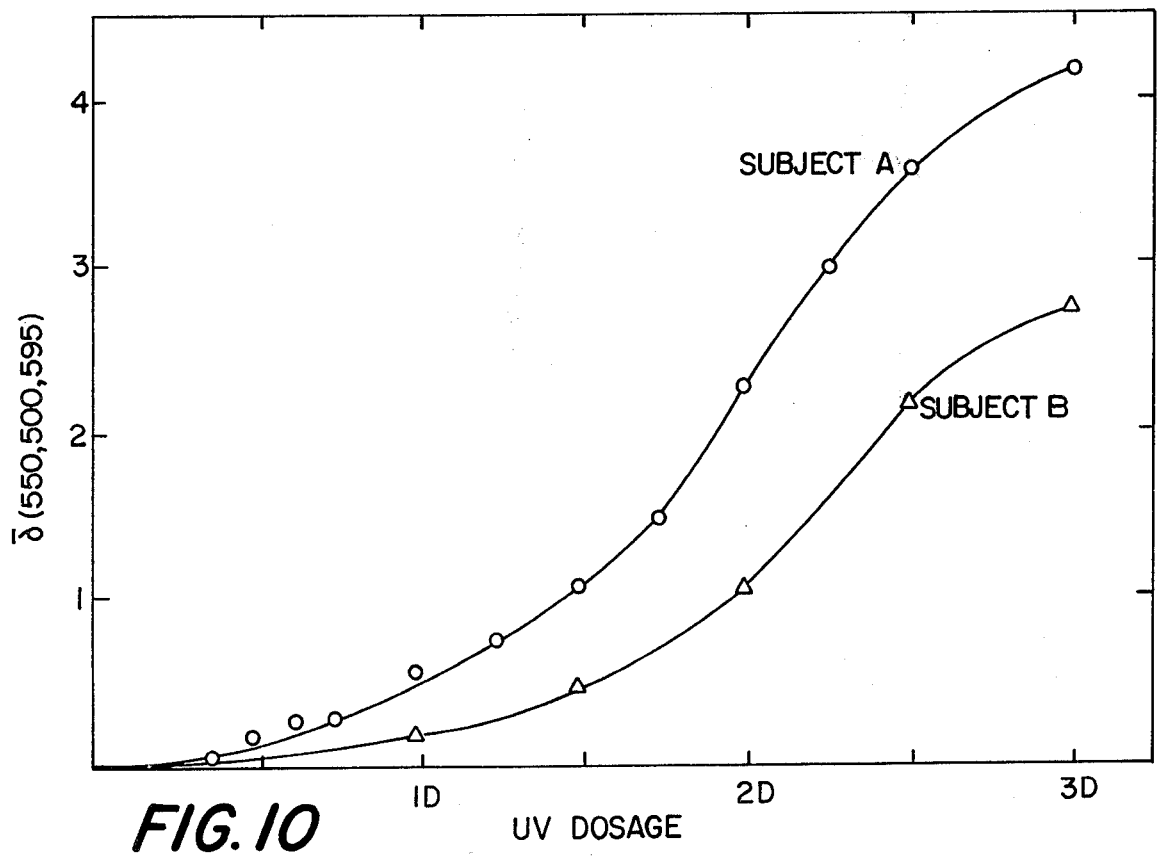
FIG. 10 shows three wavelength erythema parameter, $\overline{\delta}(500 \text{ nm}, 550 \text{ nm}, 595 \text{ nm})$, as a function of ultraviolet dosages.

Experimental results for a specific triple-wavelength parameter, $\bar{\delta}(550,500,595)$, are presented in FIG. 10. These three wavelengths were selected in accordance with the above stated requirements.

FIG. 10 shows the dosage dependence of the $\bar{\delta}(550,500,595)$ parameter for two subjects; subject A is the same individual previously discussed. The dosage dependence of $\bar{\delta}$ observed in the figure has the same shape as that determined using the two-wavelength $\bar{\delta}$ parameter, as anticipated. Moreover, the $\bar{\delta}(550,500,595)$ experimental values for subject A fall between the $\bar{\delta}(540,510)$ and $\bar{\delta}(560,595)$ response limits as expected for the absolute response values. The results demonstrate that the triple-wavelength parameter, $\bar{\delta}(500,550,595)$, effectively eliminates the influence of skin pigmentation from the skin reflectance measure of erythema. This function therefore establishes an absolute scale for the evaluation of the vascular response of the skin due to ultraviolet irradiation. Specifically, a 25 percent ($\bar{\delta}=0.25$) increase in blood volume is observed for the minimal perceptible erythema site (0.75 D) of subject A while the site exhibiting a minimal perceptible erythema with clearly defined boundaries (1 D) corresponds to a 50 percent increase in blood volume. The maximum ultraviolet dosage (3 D) used in this study elicited a more than four-fold increase in superficial blood volume for this subject.

Subject B was found to have a higher tolerance to the ultraviolet irradiation than subject A. This was somewhat unexpected since subject B is lighter complexioned than subject A. For subject B, a two minute ultraviolet exposure (1 D) was required to produce a minimal perceptible erythema twenty-four hours after irradiation. This minimal perceptible response was found to correspond to a 20 percent increase in blood volume ($\bar{\delta}=0.20$) as shown in FIG. 10. The fact that a smaller increase in blood volume was required to produce a minimal perceptible erythema for subject B is attributed to the lesser melanin content of this individual; increased melanin content tends to obscure the visually perceptible effect of vasodilation.

The implications of the establishment of an absolute scale for evaluation of erythema based upon the change in skin reflectance are quite exciting. This definitive measure will enable characterization of erythema with precision and reproducibility previously not possible. While currently the MED provides the only consistent reference measure of erythema, the skin reflectance relation establishes a continuous scale for defining degree of erythema; in fact, the skin reflectance measure is sensitive enough to distinguish vascular effects too subtle to be observed visually. This also suggests that the objective skin reflectance measure can replace the subjectively determined MED measure of the skin's tolerance to ultraviolet light; for instance, incremental dosages can be administered to establish the dosage required to elicit a 50 percent increase in superficial blood volume. Thus, evaluation of erythema by skin reflectance analysis has strong potential as a research tool to provide detailed fundamental information concerning the effects of ultraviolet radiation upon the skin as well as providing the basis for a clinical device for critical evaluation of individual erythemal responsivity.

The function $\bar{\delta}(550,500,595)$ is the now known best optimal relation for evaluation of erythema. However, other wavelength combinations might be utilized; but it is not anticipated that increased spectral resolution will significantly influence results, however.

Since erythema transient response can be related to skin-cancer susceptibility, the establishment of a procedure for critical evaluation of erythema response has taken on added significance. To demonstrate the utility of the skin reflectance analysis method in this context, a serial investigation was performed and representative data acquired. The skin reflectance at three test sites on the subject in the preceding study was monitored at twenty-four hour intervals for a period of fifteen days following the initial ultraviolet exposure. Experimental results for the three dosage levels are presented in FIG. 11 where the reflectance data has been transformed to represent the relative increase in superficial blood volume through the parameter $\bar{\delta}(550,500,595)$ as dictated by the physical model.

Figure 11:
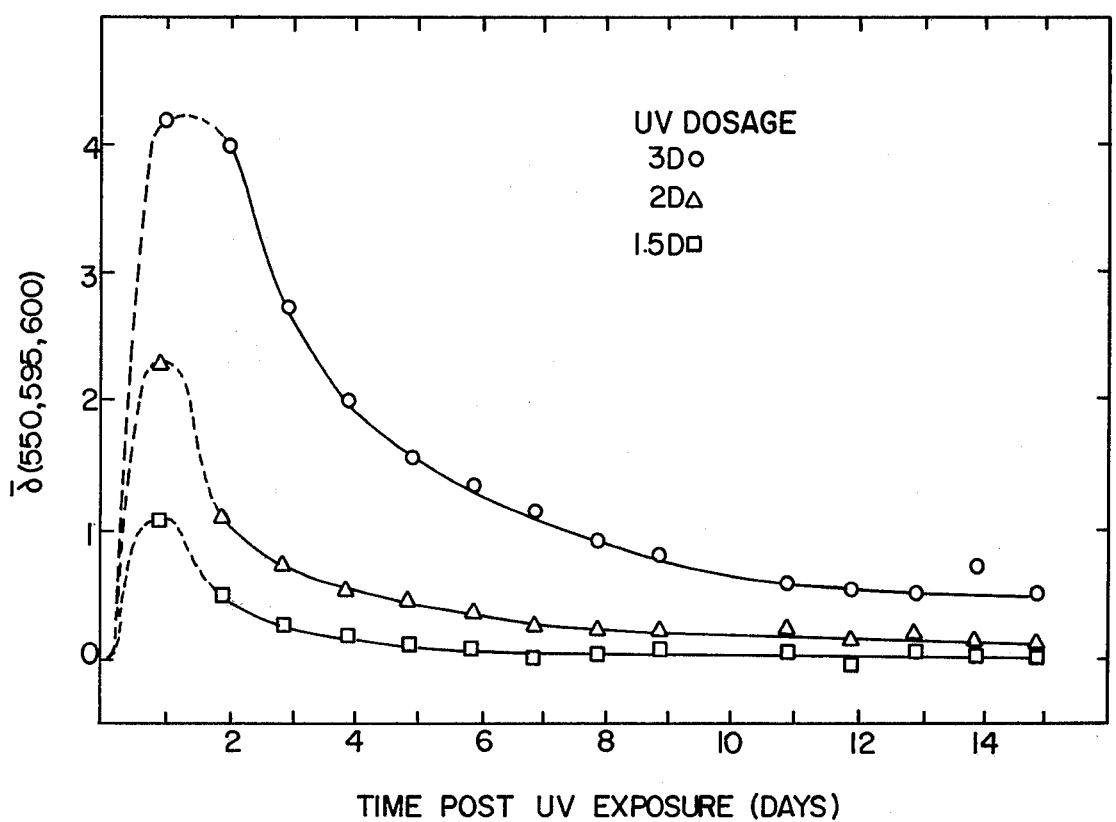
FIG. 11 shows three wavelength erythema parameter, $\overline{\delta}(500 \text{ nm}, 550 \text{ nm}, 595 \text{ nm})$, as a function of time for three ultraviolet dosages.

The experimental results of FIG. 11 demonstrate the vascular response of the skin resulting from ultraviolet irradiation. There is a sharp increase in superficial blood volume within twenty-four hours after ultraviolet exposure with an asymptotic regression of the effect occurring over a period of days; a stronger ultraviolet dose produces a greater dilating effect which regresses over a correspondingly longer interval. For the limited amount of data acquired, it is improper to attempt a detailed interpretation of the early time response; the dashed lines used in the early portion of the response curves are intended to indicate this uncertainty. Although the dashed curves represent a possible time course, it is improbable that these approximations accurately depict the true progression. Later values on the response curves may be interpreted with considerable confidence, however, and are represented by the solid lines. By the fifteenth day, the optical parameter indicates that the influence of the two higher level ultraviolet dosages has not completely subsided. It is not clear whether some quasi-permanent vascular change has taken place or if the influence of melanin has not been completely removed and a tanning bias is present. The fact that the curves continue to decrease tends to support the former premise; however, if the latter is the case, the effect is relatively small. The experimental reflectance results are consistent with the relative reflectance data of solar erythema reported by others. The model transformation, however, modifies the appearance of the response curve and converts the reflectance values to a quantitative, physiologically meaningful quantity which is independent of individual skin pigmentation characteristics.

The method of this invention allows screening of individuals to determine their sensitivity to ultraviolet radiation; evaluation of sun screening agents with quantitative evaluation of the efficacy of commercial products of this nature; screening of individuals for susceptibility to skin irritation and therefore skin cancer; and/or screening of individuals for sensitivity to specific irritants including chemicals, allergens, ansynetics, soaps/detergents, and clothing.

It should therefore be apparent from the foregoing that this invention provides a new and novel method for evaluating erythema utilizing skin reflectance measurements.

What is claimed is:

1. A method for determining erythema, said method comprising:
    establishing a predetermined physiologic measure based upon blood content with respect to a patient;
    exposing the skin of said patient to radiation and collecting said radiation reflected from said skin;
    utilizing said collected radiation to provide an indication of skin reflectance measure; and
    relating said indication of skin reflectance measure to said predetermined physiologic measure to thereby provide an indication of the extent of erythema with respect to the skin of said patient.

2. The method of claim 1 wherein said step of establishing a predetermined physiologic measure includes providing an absolute scale and wherein said step of relating said indication of skin reflectance measure to said predetermined physiologic measure includes utilizing said absolute scale to relate said predetermined physiologic measure to said indication of skin reflectance measure.

3. The method of claim 1 wherein said step of exposing the skin of said patient to radiation and collecting said radiation reflected from said skin includes exposing the skin of said patient to radiation at a plurality of predetermined wavelengths and utilizing the collected radiation at each of said plurality of wavelengths to provide said indication of skin reflectance measure.

4. The method of claim 3 wherein said step of exposing the skin of said patient to radiation at a plurality of predetermined wavelengths includes exposing the skin of said patient to radiation at a minimum of three different wavelengths.

5. The method of claim 4 wherein said step of exposing the skin of a patient to radiation at a minimum of three different wavelengths includes exposing the skin of said patient to radiation at about 500 nm, 550 nm, and 595 nm.

6. The method of claim 1 wherein said method includes directing said radiation to a reference standard to thereby collect radiation reflected from said reference standard as well as from said exposure of the skin of said patient to said radiation so as to provide an absolute erythema measure.

7. A method for definitive evaluation of erythema by multi-spectral skin reflectance analysis, said method comprising:
    establishing an absolute physiologic measure based upon blood content with respect to a patient and forming output signals representative thereof;
    directing radiation at a predetermined plurality of wavelengths at the skin of a patient;
    collecting said radiation reflected from the skin of said patient at said predetermined wavelengths and providing therefrom output signals indicative of the reflectance of said skin; and
    relating said output signals from said collected radiation to said output signals representative of said established absolute physiologic measure to thereby form an evaluation of erythema then present at the skin of said patient.

8. The method of claim 7 wherein said step of directing radiation at a predetermined plurality of wavelengths at the skin of a patient includes directing radiation at at least three different wavelengths at the skin of a patient, and wherein said step of collecting radiation includes collecting said radiation reflected from the skin of said patient at said three different wavelengths.

9. The method of claim 8 wherein said step of directing radiation at at least three different wavelengths at the skin of a patient includes directing radiation at 500 nm, 550 nm, and 595 nm at the skin of a patient, and wherein said step of collecting radiation includes collecting said radiation from said patient at said three wavelengths.

10. A method for evaluation of erythema present at the skin of a patient, said method comprising:
   establishing a relationship between skin reflectance and skin absorption and scattering properties;
   measuring skin reflectance of both normal and erythematous skin;
   determining from said established relationship and said skin reflectance measurements the blood volume due to erythema; and
   utilizing said determination of blood volume to indicate the extent of erythema.

11. The method of claim 10 wherein said step of establishing a relationship between skin reflectance and skin absorption and scattering properties includes establishing said relationship between skin reflectance and skin absorption and scattering properties at a plurality of at least three separate wavelengths.

12. A method for determining erythema, said method comprising:
   establishing an erythema parameter that is a function of normal and erythematous skin reflectance at 500 nm, 550 nm, and 595 nm;
   exposing the skin of a patient to ultraviolet radiation;
   collecting ultraviolet radiation reflected from the skin of said patient at wavelengths of 500 nm, 550 nm, and 595 nm; and
   relating said collected ultraviolet radiation with said established erythema parameter to derive therefrom the extent of erythema present at the skin of said patient.

13. The method of claim 12 wherein said method includes utilizing said determined extent of erythema to determine application of dosage of electromagnetic radiation to the skin of said patient.

14. The method of claim 12 wherein said method includes applying a substance to the skin of said patient prior to collecting of reflected radiation from the skin of said patient and determining therefrom the effectiveness of said substance with respect to erythema.

15. The method of claim 12 wherein said method includes periodically collecting radiation reflected from the skin of said patient and deriving the extent of erythema therefrom to thereby provide treatment data.

* * * * *